United States Patent [19]

Levin

[11] 4,263,919

[45] Apr. 28, 1981

[54] HEARTBEAT DETECTION AND ARTIFACT DISCRIMINATION METHOD AND APPARATUS

[76] Inventor: Kenneth M. Levin, 14 Anchorage Ct., San Rafael, Calif. 94903

[21] Appl. No.: 84,473

[22] Filed: Oct. 12, 1979

[51] Int. Cl.³ .............................................. H61B 5/04
[52] U.S. Cl. .................................... 128/708; 128/901
[58] Field of Search ............... 128/696, 697, 698, 702, 128/704, 703, 708, 901, 902

[56] References Cited

U.S. PATENT DOCUMENTS

| | | | |
|---|---|---|---|
| 3,533,402 | 10/1970 | Siedband | 128/703 |
| 3,590,811 | 7/1971 | Harris | 128/708 |
| 3,709,212 | 1/1973 | Koeblitz | 128/902 |
| 4,112,930 | 9/1978 | Feldman et al. | 128/704 |

*Primary Examiner*—William E. Kamm
*Attorney, Agent, or Firm*—Townsend and Townsend

[57] ABSTRACT

Apparatus for discriminating between heartbeat and artifact information contained in an ECG signal includes a pair of difference amplifiers, level-detecting circuitry and a coincidence detector. ECG waveforms are obtained from a number of heartbeat-sensing transducers attached to a person. The waveforms are individually applied to a pair of difference amplifiers to produce difference signals containing heartbeat information. The difference signals are applied to level-detecting circuits and compared to predetermined voltage levels to identify particular peaks indicative of a heartbeat. The result of the level-detecting circuits are compared for time coincidence to produce an output pulse indicative of a heartbeat.

8 Claims, 10 Drawing Figures

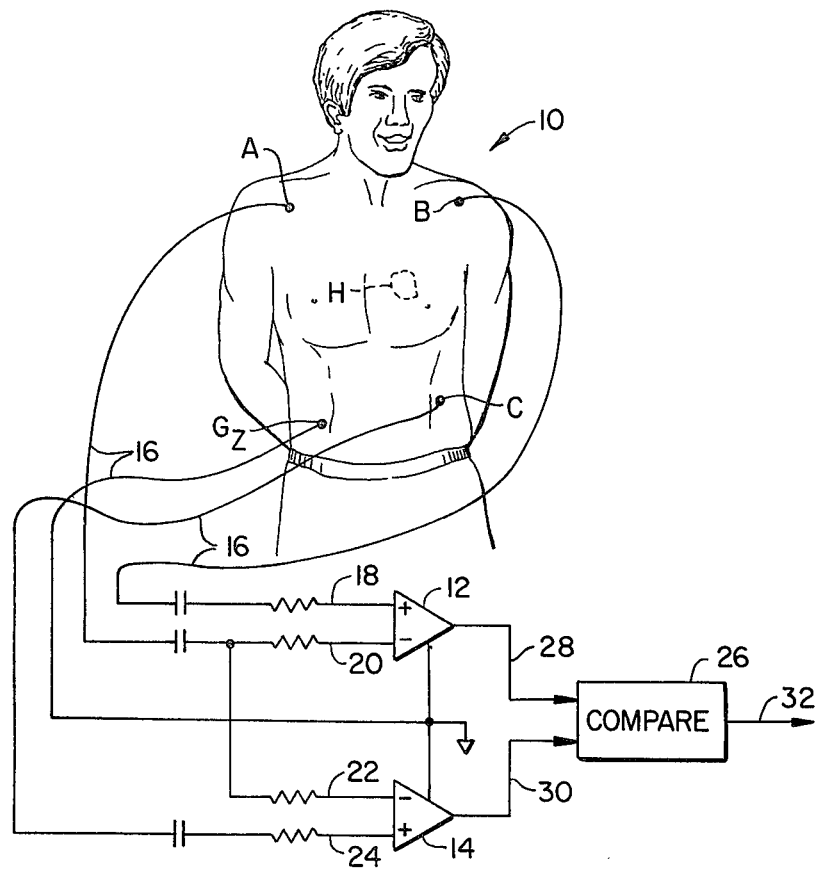
FIG._1.
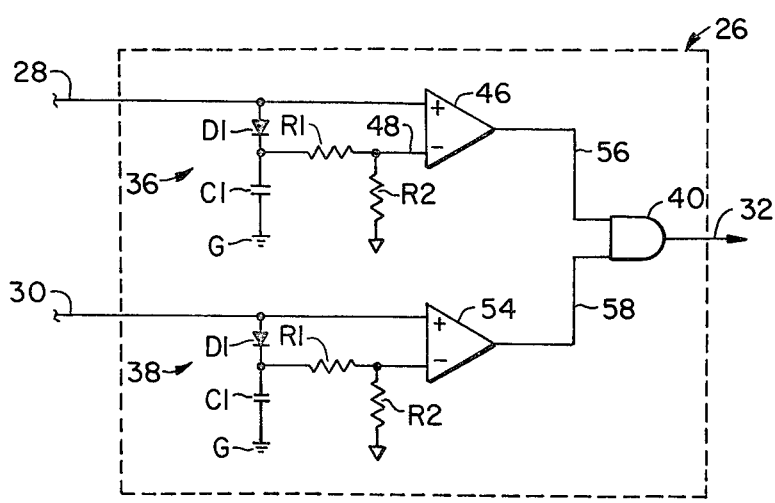
FIG._2.

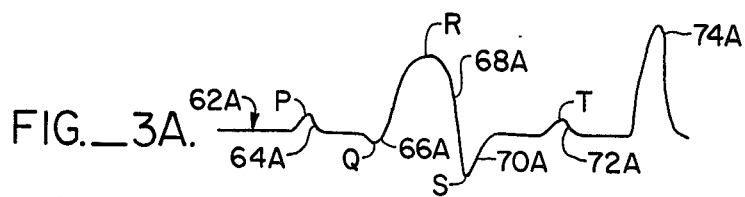
FIG._3A.
FIG._3B.
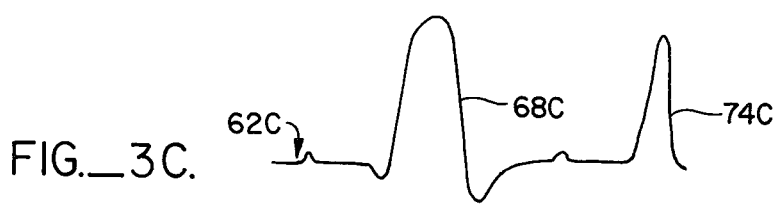
FIG._3C.
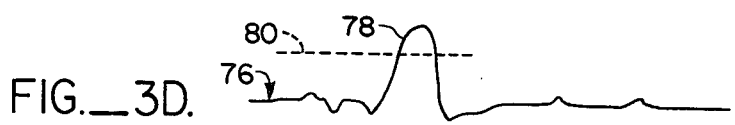
FIG._3D.
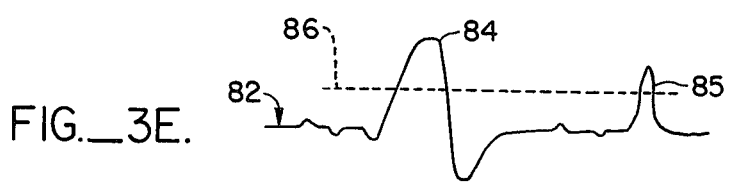
FIG._3E.
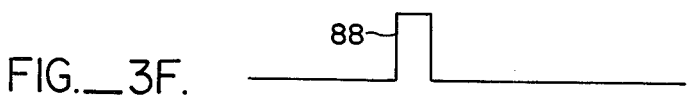
FIG._3F.
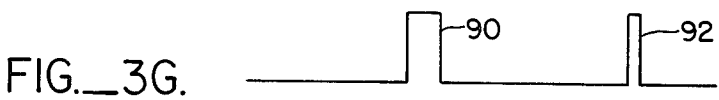
FIG._3G.
FIG._3H.

HEARTBEAT DETECTION AND ARTIFACT DISCRIMINATION METHOD AND APPARATUS

The present invention relates to a method and apparatus for monitoring cardiac-produced electrical signals and more particularly to a device that discriminates undesirable artifact signals from electrocardiographic signals to produce an output indicative of heartbeat occurrence.

BACKGROUND OF THE INVENTION

It is well known that expansion and contractions of muscle produce electrical signals that circulate upon the surface of a person's skin. Perhaps the most common are the expansions and contractions of the cardiac muscle, which produce electrical signals typically referred to as ECG signals. These ECG signals exhibit particular waveforms containing several distinct characteristics for each heartbeat. These characteristics, generally labeled P, Q, R, S and T, according to common medical usage, have allowed medical science to monitor a person's electrocardiogram and thus determine the heartrate.

Each heartbeat will produce an ECG signal that typically includes three "positive" peaks, labeled the P, R and T peaks. Usually, it is the R peak that is the largest of these three positive peaks. Since it is necessary that only one peak be detected for each heartbeat, a threshold detector can be employed in the simple case to distinguish between P and T waves, on the one hand, and R waves on the other. Accordingly, the R-wave peaks are available and often used to trigger the threshold detector to generate heartbeat count.

As noted at the outset, all muscle tissue will emit electrical signals when expanding or contracting, the heart being only one of the many muscle groups of a person's body. Thus, when a person is in motion, such as when exercising, the problem of monitoring the person's heartbeat by identifying particular characteristics of ECG waveforms becomes extremely difficult; the reason being that sensors placed on the person to detect the ECG signal also receive electrical signals, typically termed "artifact", produced by the other expanding and contracting muscles of the body. Often such artifact signals in the ECG waveform bear a marked resemblance to the R-wave peaks.

Under such circumstances, the practice of limiting the frequency response characteristics of the ECG waveform and/or rejecting artifact by amplitude discrimination or pulse width discrimination to identify each heartbeat has been found to be generally insufficient, even when these techniques are used in combination. Accordingly, in order to limit the artifact signals, produced when a person is in motion, it is desirable that the person remain relatively motionless while an ECG waveform is being obtained—particularly if the fidelity of the desired ECG waveform is to be as accurate as possible.

Yet, it is desirable that persons have the capability of somehow monitoring their heartbeat—primarily heartbeat rate— while in motion. For example, one may wish to stress one's cardiovascular system within predetermined limits through exercise that produces cardiac activity (i.e., a heartbeat rate) greater than a predetermined minimum, yet less than a specified maximum. Of course, one could always cease exercising periodically and monitor heartbeat rate by monitoring his or her pulse. However, this technique is bothersome if exercise is to be sustained for any length of time (by jogging, for example) and can fail to warn one when cardiac activity reaches or exceeds a dangerous level during exercise.

Therefore, it is desirable that additional techniques be found to allow the identification of each heartbeat occurrence in an ECG signal produced while a person is, for example, exercising, so that such identification can, in turn, be used to provide accurate monitoring of a person's heartbeat. This is particularly true if the person wishes to exercise his or her cardiovascular system, yet maintain a heartbeat rate that is within predetermined limits.

SUMMARY OF THE INVENTION

The present invention, therefore, provides a method and apparatus that discriminates between artifact and heartbeat occurrence contained in ECG signals produced by a person. The invention allows the heartbeat to be detected even in the presence of artifact signals contained in the ECG waveforms, produced by movement of the person such as, for example, while exercising.

According to the present invention, ECG waveforms obtained from a number of heartbeat-sensing transducers placed at various locations on a person are applied to at least a pair of difference amplifiers. Each difference amplifier algebraically subtracts one electrical signal applied thereto from the other, amplifies the difference, to produce a difference signal containing heartbeat information. At the same time, however, artifact information transmitted by muscle groups remote from the two heartbeat-sensing transducers coupled to the difference amplifier is removed by the common-mode rejection characteristics of the difference amplifiers. The difference signals produced by each difference amplifier are compared for heartbeat coincidence to produce an output pulse indicative of such heartbeat occurrence.

In the preferred embodiment, four heartbeat-sensing transducers are used, three of which obtain an ECG signal relative to the fourth (reference) transducer. The ECG signals obtained by first and second ones of the heartbeat-sensing transducers are applied to a first difference amplifier to obtain a first difference signal. Similarly, the ECG signals obtained by the first and third heartbeat-sensing transducers are applied to a second difference amplifier to produce a second difference signal. The two difference signals so obtained are applied to level-detecting circuitry to identify particular peaks of the difference signals such as, for example, the R-wave peak. The level-detecting circuits will produce a specified output pulse when the amplitude of the signal applied thereto exceeds an assigned D.C. value. The output pulse of each level-detecting circuit is communicated and applied to a coincidence gate which compares the pulses produced by the level-detecting circuits for time coincidence. When coincidence is achieved, the coincidence gate produces an output pulse indicative of heartbeat occurrence. The output pulse so generated can be used to monitor heartbeat rate by appropriate rate monitoring apparatus.

Thus, as will be more apparent after reading the detailed description of the invention below, the present invention provides a number of advantages. For example, the invention operates to reject troublesome artifact that can seriously impair or otherwise obscure attempts to monitor heartbeat rate. Artifact produced by muscle groups remote from a heartbeat-sensing transducer pair is removed from the ECG signals produced by transducer pair by the common-mode rejection characteristics of the difference amplifier to which the ECG signals are applied. Any remaining artifact—artifact not remote to a heartbeat-sensing transducer so that the two ECG signals applied to a difference amplifier will produce an artifact signal—will be rejected by level-detecting each difference signal and comparing the outputs of the level-detecting circuits for time coincidence.

Further, the simplicity of the technique incorporated by the present invention allows its use in combination with other artifact-discriminating circuits to provide further reliability. For example, the ECG signals obtained by the transducers may be preamplified before applied to the difference amplifiers. This preamplification step can include frequency limiting techniques. Alternatively, the difference amplifiers themselves may be designed with a predetermined bandwidth to provide frequency limiting of the ECG signal, thereby reducing or minimizing artifact activity.

These and other advantages of the present invention, as well as a fuller understanding of the nature and advantages of the invention, will be had after reference is made to the ensuing detailed description taken in conjunction with the accompanying drawings.

BRIEF DESCRIPTION OF THE DRAWINGS

FIG. 1 is a block diagram of the artifact-discriminating apparatus of the present invention illustrating its attachment to a person for obtaining an ECG signal from which a heartbeat occurrence indicia pulse is obtained;

FIG. 2 is a block diagram of the compare circuit of FIG. 1; and

FIGS. 3A–3H illustrate typical waveforms involved in the operation of the apparatus of FIGS. 1 and 2.

DETAILED DESCRIPTION OF THE DRAWINGS

An illustrative embodiment of the invention, in partial block diagram form, is shown in FIG. 1. Standard heartbeat-sensing transducers A, B, C and $G_z$ are attached to the skin of the person 10 for picking up the varying cardiac potential produced by heartbeat activity. The heartbeat-sensing transducers A, B, C and $G_z$ are coupled to difference amplifiers 12 and 14 via electrical leads 16. Heartbeat-sensing transducer B is applied to the positive input 18 of difference amplifier 12, while the heartbeat-sensing transducer A is coupled to the negative input 20 thereof. Similarly, heartbeat-sensing transducers A and C are coupled to the negative and positive inputs 22 and 24, respectively, of difference amplifier 14. The heartbeat transducer $G_z$ is coupled to both difference amplifiers 12 and 14 and used as a reference for the signals produced by heartbeat-sensing transducers A, B and C.

The difference amplifiers 12 and 14 algebraically subtract the ECG signals applied to their respective negative inputs 20 and 24 from those applied to their positive inputs 18 and 22. The differences are amplified by each difference amplifier 12 and 14 and communicated to a compare circuit 26 via output lines 28 and 30. The compare circuit 26 monitors the two difference signals communicated thereto to identify a predetermined characteristic of each signal and to determine the time coincidence of occurrence of such characteristics. This determination is indicative of heartbeat occurrence and an output pulse is produced by the compare circuit 26 on signal line 32.

The embodiment of compare circuit 26, which is presently preferred, is shown in FIG. 2 as including peak detector circuits 36 and 38 and a coincidence (AND) gate 40. Both peak detector circuits 36 and 38 are essentially identical in structure and function. Accordingly, like reference designations will be used for like elements and only the peak detector circuit 36 will be described, it being understood that such description being applied equally to the peak detector circuit 38. Any differences between the two peak detector circuits 36 and 38 will, of course, be noted.

The peak detector 36 includes a comparator 46 to which is coupled the output of difference amplifier 12 via output line 28. A DC level-setting circuit, comprising diode D1, voltage divider resistors R1 and R2, and capacitor C1, interconnects the output line 28 to the positive input of comparator 46. The resistors R1 and R2 interconnect diode D1 with the reference (signal) ground (indicated in FIGS. 1 and 2 by the inverted triangle signal) established by the heartbeat-sensing transducer $G_z$. The capacitor C1 interconnects the diode D1 with circuit ground G. This level-setting circuit operates to hold the output line 28 at a predetermined DC level. When the signal provided by difference amplifier 12, and appearing on output line 28, exceeds this predetermined DC level, the comparator 46 (as will comparator 54) will generate a (positive) pulse.

The DC levels for peak detectors 36 and 38 are set by the threshold voltage of diodes D1 in combination with the voltage divider networks formed by resistors R1 and R2. Capacitor C1 functions to expand the width of narrower signals received on the output lines 28 and 30.

Output lines 56 and 58 communicate the output of each level detector 36 and 38 to the coincidence gate 40 where the results are compared for time coincidence to produce a pulse indicative of such coincidence on output line 32.

In operation, the heartbeat-sensing transducers A, B and C are attached to the chest of the person 10 as illustrated in FIG. 1. For best performance, the orientation of heartbeat-sensing transducers A, B and C should be such that a different ECG lead configuration is used on each pair of heartbeat-sensing transducers that are differentially combined via the differential amplifiers 12 and 14. As used here, the term "lead" is meant to refer to placement of a pair of heartbeat-sensing transducers on a person's body and with respect to the person's heart such as, for example, the classical ECG placements known as lead I, lead II, and lead III (In FIG. 1, heartbeat-sensing transducers A and B form a classic lead I configuration while heartbeat-sensing transducers A and C form a lead II configuration). The reference heartbeat-sensing transducer $G_z$ can be placed anywhere on the person's chest, but preferably physically spaced from the heartbeat-sensing transducers A, B and C. The ECG signal obtained by each of the heatbeat-sensing transducers A, B and C is, in effect, the potential difference between each transducer A, B and C and the reference transducer $G_z$.

So attached, the heartbeat-sensing transducers will detect electrical events produced by heartbeat activity, as well as other muscle activity, and communicate the detected events as electrical signals to the difference amplifiers 12 and 14 via the electrical lines 16. For example, FIGS. 3A–3C illustrate representative ECG waveforms 62A, 62B and 62C that may be provided by heartbeat-sensing transducers A, B and C, respectively. The waveforms illustrated are drawn so that the vertical dimension represents voltage amplitude while the horizontal dimension represents time, with time increasing as the waveform proceeds to the right. The waveforms and their phase relationships are exaggerated somewhat to illustrate the operation of the invention.

The representative ECG waveform 62A, produced by the heartbeat-sensing transducer A, is shown as including the PQRST complex wave peaks 64A, 66A, 68A, 70A and 72A, respectively. Additionally, the waveform 62A is illustrated as containing an artifact peak 74A produced by a muscle group. Similarly, FIGS. 3B and 3C illustrate the representative waveforms 62B and 62C provided by the heartbeat-sensing transducers B and C. The waveforms 62B and 62C also contain, as can be seen, the wave peaks of the PQRST complex. Thus, for example, the ECG waveform 62B contains the wave peaks 64B, 66B, 68B, 70B and 72B. Additionally, the artifact wave peak 74A of ECG waveform 62A (FIG. 3A) appears in ECG waveform 62B (FIG. 3B) as artifact wave peak 74B; it also appears in ECG waveform 62C (FIG. 3C) as artifact wave peak 74C.

Before continuing, certain aspects of the illustrative ECG waveforms 62A-62C are worth noting. First, it will be noted that those portions of the ECG waveforms 62A-62C forming heartbeat information (i.e., the PQRST complex wave peaks) are different in magnitude. Conduction of muscle-generated electrical signals in a person's body, including heartbeat-generated signals, is volumetric (three-dimensional) in nature. The magnitude of signals produced by transducers near the source of the signal (such as heart H) will differ in magnitude from signals produced by transducers further from the source. Accordingly, the electrical events produced by cardiac activity are viewed as different amplitude signals, depending upon the relative location of the particular heartbeat-sensing transducer receiving the signal. For example, the R-wave peak 68A of ECG waveform 62A is relatively smaller in magnitude than are the R-wave peaks 68B and 68C of ECG waveforms 62B and 62C, respectively (FIGS. 3A-3C) because heartbeat-sensing transducer A is located further from the heart H than are heartbeat-sensing transducers B and C.

The differences in amplitude between R-wave peaks 68A and 68B will be differentially amplified by the difference amplifier 12 to produce the signal peak 78 illustrated in FIG. 3D. Similarly, the ECG waveforms 62A and 62C received by heartbeat-sensing transducers A and C are applied to difference amplifier 14 to produce the signal illustrated in FIG. 3E.

The ECG waveforms 62A and 62B also contain artifact signals 74A and 74B generated by activity of muscle other than the heart H. Note that the amplitude and shape of artifact signals 74A and 74B are substantially identical. The reason is that the muscle group producing the artifact 74A and 74B is located a relatively large distance from both heartbeat-sensing transducers A and B. Accordingly, volumetric conduction through the body of person 10 of the electrical signal produced by the muscle group will cause the signal to be substantially identical when received by heartbeat-sensing transducers A (as signal 74A) and B (as signal 74B). However, the electrical signal appearing at the heartbeat-sensing transducer C is different in amplitude. Because the muscle group that produces the electrical signal resulting in the artifact 74A–74C is located closer to the heartbeat-sensing transducer C (than transducers A or B), the amplitude of the signal undergoes less attenuation by the volumetric conduction of the signal through the person 10. Accordingly, there is a difference in amplitude between artifact signals 74A and 74C.

The ECG waveforms 62A-62C provided by the heatbeat-sensing transducers A-C, respectively, are applied to the difference amplifiers 12 and 14, as described above. Illustrated in FIGS. 3D and 3E are the output waveforms 76 and 82 produced by the difference amplifiers 12 and 14. Thus, for example, the output waveform 76 represents the amplified difference between the ECG waveforms 62A and 62B. The relatively large positive peak 78 of the output waveform 76 is the amplified difference between the R-wave peaks 68A and 68B of the ECG waveforms 62A and 62B. The dotted line 80 (FIG. 3D) represents the D.C. level set by the diode D1 of peak detector 36. When the positive excursions of the waveform 76 exceed the D.C. level 80, such as by the peak 78, the pulse 88 (FIG. 3F) is produced by peak detector 36 on the output line 56 and communicated to the coincidence gate 40. Note particularly that the two positive artifact peaks 74A and 74B have been substantially eliminated by the common-mode rejection characteristics of the differential amplifier 12.

In a similar manner, the output waveform 82 of FIG. 3E represents the amplified difference between the ECG waveforms 62A and 62C. The positive peak 84 of the output waveform 82 is a product of the amplified differences between the R-wave peaks 68A and 68C. The peak 84 results in generation of the pulse 90 (FIG. 3G) when applied to the peak detector 38 and the peak 84 exceeds the D.C. level set by diode D1 and illustrated in FIG. 3E by the dotted line 86. Note that the amplitude difference between the artifact wave peaks 74A and 74C contained in the ECG waveforms 62A and 62C results in the appearance in the output waveform 82 as positive peak 85. The positive peak 85 may even be of sufficient amplitude to cause the peak detector 38 to provide an output pulse 92 (FIG. 3G).

The output signals generated by peak detectors 36 and 38 are applied to coincidence gate 40 and compared for time coincidence of any simultaneously, or near-simultaneously, occurring positive pulses. If such coincidence does occur, an output pulse will be provided on output line 32 by the coincidence gate 40. Thus, for example, the near-simultaneous occurrence (in time) of the positive pulses 88 and 90 will cause, when applied to the inputs of the coincidence gate 40, the output pulse 94 (FIG. 3H) to appear on output line 38. Since the output pulse 92 was ultimately caused by the electrical event produced by a heartbeat, the output pulse 92 is indicative of such heartbeat occurrence.

Note that comparison of the output signals provided by the peak detecting circuits 36 and 38 for time coincidence of any positive pulses effectively eliminates the artifact produced pulse 92. Any artifact information not removed by the common-mode rejection characteristics of the difference amplifiers 12 and 14, in the manner described above, will be rejected by coincidence gate 40. Thus, the pulses appearing on output line 32 not only are indicative of heartbeat occurrence, but are free from troublesome artifact that can be produced when a person is moving such as, for example, when exercising.

In summary, therefore, there has been disclosed apparatus capable of discriminating between electrical signals produced by cardiac activity from those produced by other muscle or motion activity to produce therefrom an output signal indicative of each heartbeat occurrence. Such a signal is ideally suited for use by apparatus monitoring heartbeat rate or R-wave peak intervals.

While the above provides a full and complete disclosure of the preferred embodiments of the invention, various modifications, alternate constructions and equivalents may be employed. For example, the waveforms 76 and 82 produced by difference amplifiers 12 and 14 could be compared by summing the two waveforms and applying the resultant summation to level or peak-detecting circuitry. It is believed that hereby, an output indicative of heartbeat occurrence could be obtained. However, this summing technique would not work if the artifact signal is exceptionally large relative to the ECG signal. Further, the number of heartbeat-sensing transducers placed on the person 10 can be increased, with the circuitry of FIGS. 1 and 2 increased proportionately, to a point so that it would theoretically be possible to literally jump up and down on the person 10 and still receive reliable R-wave to R-wave period information. Therefore, the above description and illustrations should not be construed as limiting the scope of the invention, which is defined by the appended claims.

What is claimed is:

1. Apparatus for discriminating between heatbeat and artifact information contained in electrocardiographic signals obtained from at least three transducer means attached to a person, the apparatus comprising:
   first difference amplifying means for receiving said electrocardiographic signals from two of said transducer means, for amplifying the said signals, and for producing therefrom a first difference signal;
   second difference amplifying means for receiving said electrocardiographic signals from one of the said first named two transducer means and from a third one of said transducer means, for amplifying said signals, and for producing therefrom a second difference signal; and
   means for receiving the produced first and second difference signals and responsive to coincidence therebetween to produce an output signal indicative of heartbeat occurrence.

2. The apparatus of claim 1, wherein said coincidence means includes level-detecting means for detecting waveform excursions of said first and second difference signals beyond at least one predetermined D.C. level.

3. The apparatus of claim 1, including first and second level-detecting means respectively interconnecting said first and second difference amplifying means and said coincidence means for detecting excursions of said first and second coincidence signals beyond at least one predetermined D.C. level.

4. The apparatus of claim 3, wherein said coincidence means includes AND gate means responsive to said first and second peak-detecting means for producing a heartbeat signal indicative of heartbeat occurrence when coincidence between said first and second difference signals is determined by said AND gate means.

5. The apparatus of claim 1, including fourth transducer means attached to said person, means for coupling said fourth transducer means to said first and second difference amplifying means for use as a reference signal.

6. The apparatus of claim 1, wherein said two of said transducer means are attached to said person at locations defining an ECG lead I configuration; and said third one of said transducer means is attached to said person to form with said one of said first named two transducers an ECG lead II configuration.

7. Apparatus for detecting a heartbeat occurrence of a person and for producing therefrom an output signal indicative of said heartbeat occurrence, said apparatus comprising:
   at least three transducer means adapted to be coupled to said person for receiving electrical signals indicative of said heartbeat occurrence and for providing first, second and third electrocardiographic signals therefrom;
   difference amplifying means responsive to said transducer means for producing first and second difference signals respectively indicative of the difference between said first and second and said first and third electrocardiographic signals;
   detecting means coupled to said difference amplifying means for receiving said first and second difference signals and for respectively generating third and fourth signals indicative of said amplitude excursions of said first and second difference signals through at least a first predetermined voltage level; and
   compare means coupled to said detecting means means and responsive to time coincidence between said third and fourth signals for producing therefrom said output signal.

8. A method for discriminating between artifact and heartbeat information contained in ECG signals obtained from at least three heartbeat-sensing transducer means attached to a person and for producing therefrom an output signal indicative of a heartbeat occurrence, the method comprising the steps of:
   amplifying the difference between ECG signals obtained from two of said transducer means to produce therefrom a first difference signal;
   amplifying the difference between ECG signals obtained from one of said first named two transducer means and a third one of said transducer means to produce therefrom a second difference signal;
   detecting excursions of said first and second difference signals beyond a predetermined D.C. level; and
   responding to coincidence in time of excursions of said first and second difference signals beyond said predetermined D.C. level of said detecting step to produce therefrom said output signal.

* * * * *